United States Patent [19]

Prahl

[11] 4,381,769
[45] May 3, 1983

[54] PROTECTIVE ELEMENT FOR PRODUCING THE CLOSURE EDGES OF PLASTER BANDAGES ON THE HUMAN BODY, AND A PLASTER BANDAGE MADE USING SUCH PROTECTIVE MEMBER

[75] Inventor: Jan Prahl, Rullstorf, Fed. Rep. of Germany

[73] Assignee: IPOS Gesellschaft für integrierte Prothesen-Entwicklung und orthopädietechnischen Service mbH & Co. KG, Lüneburg, Fed. Rep. of Germany

[21] Appl. No.: 294,973

[22] Filed: Aug. 21, 1981

[30] Foreign Application Priority Data

Aug. 22, 1980 [DE] Fed. Rep. of Germany ....... 3031668

[51] Int. Cl.³ .............................................. A61F 5/04
[52] U.S. Cl. .................................................. 128/91 R
[58] Field of Search ............... 128/91 R, 90, 83, 89 R, 128/82

[56] References Cited

U.S. PATENT DOCUMENTS 3,826,252  7/1974  Laico ................................. 128/91 R Primary Examiner—John D. Yasko
Attorney, Agent, or Firm—Toren, McGeady and Stanger

[57] ABSTRACT

The invention relates to a protective element for making the closure edges of plaster bandages on the human body, the protective element consisting of a sleeve-like, flexible sectional element, one of whose edge zones has an outwardly directed folded-over closure and which has on its outer wall surface a knob-like engagement section, thus improving the making of the closure edges of plaster bandages and simplifying the production of such closure edges in plaster bandages.

2 Claims, 5 Drawing Figures

PROTECTIVE ELEMENT FOR PRODUCING THE CLOSURE EDGES OF PLASTER BANDAGES ON THE HUMAN BODY, AND A PLASTER BANDAGE MADE USING SUCH PROTECTIVE MEMBER

The invention relates to a protective element for making the closure edges of plaster bandages on the human body, and to a plaster bandage made using such protective element.

BACKGROUND OF THE INVENTION

When limbs of the human body are put in plaster, it is considered to be particularly difficult to make the closure edges. Of course the part of the body is covered by a knitted woollen tube, over which the plastic bandage is applied. When the or each closure edge is produced, it must be modelled in a round shape. When the closure edge is modelled round, it is often inevitable that small pieces of plaster slide into the plaster envelope, and this may subsequently cause chafing to the part of the body.

The knitted tube, which is plastered-in more particularly to ventilate the plaster bandage, is rigidly connected thereto precisely in the edge zones and cannot properly serve its actual original purpose. In addition, making a clean closure edge requires a relatively large amount of medical experience and skill. However, precisely the making of the closure edges takes a great deal of time.

PROBLEM

In contrast, it is an object of the invention to provide a protective element which obviates the disadvantages resulting from making the closure edges of plaster bandages and which can be so produced, reducing the time required for making the closure edges of plaster bandages, that chafing of the part of the body is prevented.

To solve this problem the invention proposes a protective element for making the closure edges of plastic bandages on the human body, the protective element according to the invention consisting of a sleeve-like flexible sectional element having a folded-over closure which is formed on one of its two circularly extending edges, the sectional element having a knob-like engagement section on its outer wall surface.

The invention also provides a plaster bandage applied to the human body and having a knitted tube bearing against the inner wall surface of the plastic sleeve, wherein the plaster sleeve of the plaster bandage has in the zone of each end-side closure edge a sleeve-like, flexible sectional element which is anchored in the plaster bandage by means of a knob-like engagement section formed on its outer wall surface and has an outwardly directed, folded-over closure which engages around the closure edge of the plaster sleeve, the inside knitted tube being folded over outwardly in the zone of the sleeve-like sectional element and being securely positioned in the plaster bandage.

The invention also provides the use of a sleeve-like, flexible sectional element as a protectional element for making the closure edges of plaster bandages on the human body, the protective element having an outwardly directed folded-over closure formed on one of its two circularly extending edges for soft edge guiding at the closure part of the plaster bandage, the protective element having formed on its outer wall surface a knob-like engagement section for making a mechanically firm connection to the plaster bandage, in order to avoid pressure places in the closure edge zone of the plaster bandage.

Due to its flexibility, a protective element constructed in this way in the form of a sleeve-like sectional element, more particularly an addition cross-linked toxicologically harmless silicon rubber, can readily be plastered into the plaster bandage to be applied. The sleeve-like sectional member or plaster sleeve is slid over the knitted tube onto, for instance, the arm, and then the plaster bandages are laid circularly around the part of the body. The knob-like engagement section on the outside of the sleeve-like sectional member enables the latter to be plastered firmly into the plaster bandage. In the direction of the inner part, the sleeve-like sectional member terminates thin, so that no pressure places can be formed between the plaster and the sectional element transition. If the plaster wall is thick enough, the knitted tube layer of the inside is folded over outwards and plastered together with the last turn of the plaster bandage into the plaster part.

At the plaster closure, therefore, a clean edge is left which both has a resilient nature and obviates impact-pressure places in the transition zone. Similarly, ventilation into the plaster is ensured by the non-plastered-in knitted tube layer at the closure of the plaster.

Further advantageous features of the invention can be gathered from the subclaims.

DETAILED DESCRIPTION OF THE PREFERRED EMBODIMENT

Figure 1:
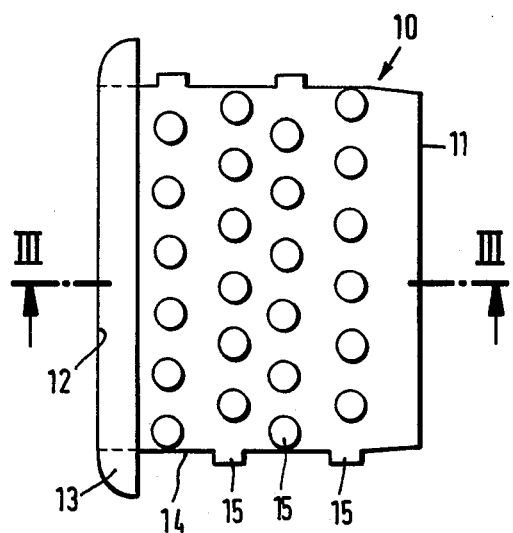
FIG. 1 is a side elevation of a sleeve-like sectional element to be worked as a protective element into plaster bandages.
Figure 3:
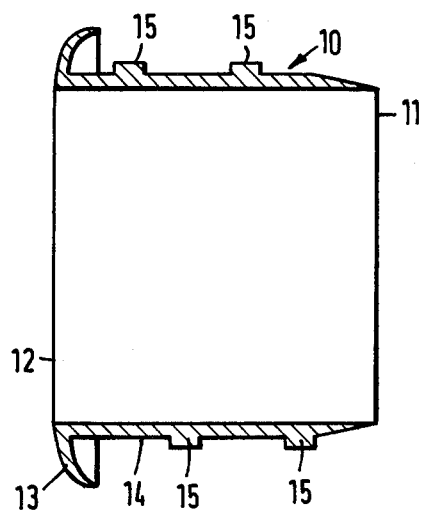
FIG. 3 is a vertical section, taken along the line III—III in FIG. 1.
Figure 2:
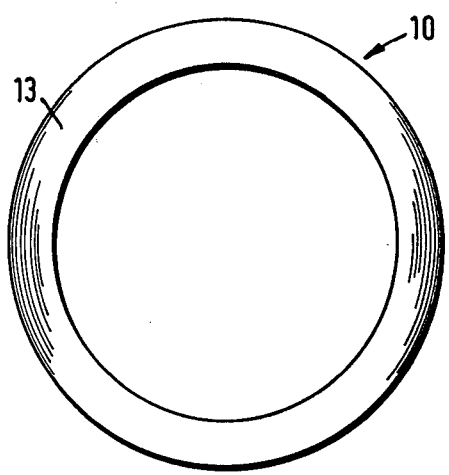
FIG. 2 is a front elevation of the sectional element.

Referring to the embodiment illustrated in FIGS. 1-3, a protective element used for making the closure edges of plaster bandages comprises a sleeve-like sectional element 10 of flexible materials, more particularly an addition cross-linked toxicologically harmless silicon rubber.

The two circularly extending end-side edges of the sectional element 10 have the references 11 and 12. An outwardly directed resilient folded-over closure 13 is formed on the circularly extending edge 12 of the sectional element 10. On its outer wall surface 14 the sectional element 10 bears a knob-like engagement section 15 which extends carpet fashion over the periphery of the sectional element. At its edge zone 11 opposite from the folded-over closure 13 the sectional element 10 tapers conically outwards (FIGS. 3).

Figure 4:
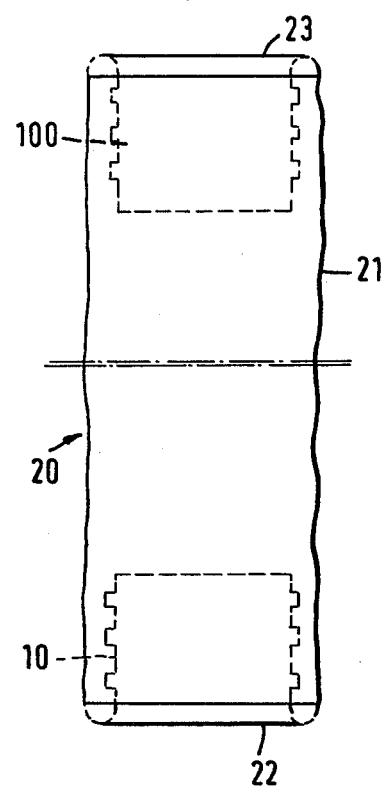
FIG. 4 is a plan view of the plaster sleeve of a plaster bandage having sleeve-like sectional elements disposed on the end side.

When a plaster bandage 20 is applied, sleeve-like sectional members 10 constructed in this way are plastered into the zone of the end-side closure edges 22, 23 of the plaster sleeve 21. In the plaster bandage 20 illustrated in FIG. 4 the bandage has a sectional element 10 and 100 plastered into the zone of each of its two end-side closure edges 22, 23. The two sectional elements 10, 100 are identically constructed. Each sectional member 10, 100 is so plastered in that its particular folded-over closure 13, forms the closure edge of the plaster bandage.

Figure 5:
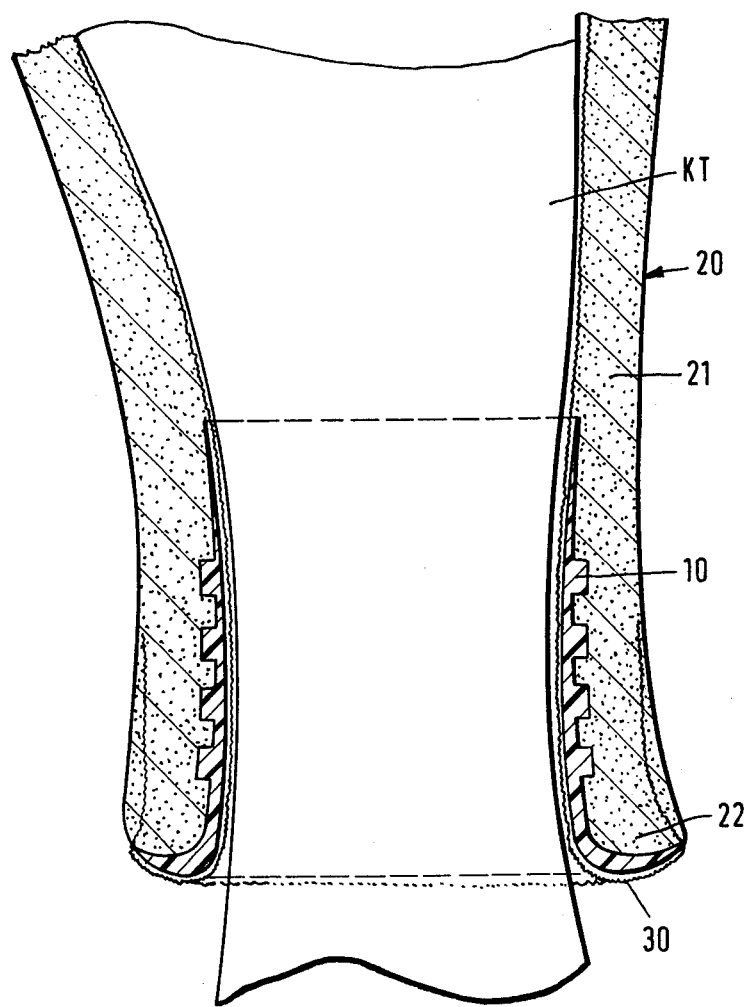
FIG. 5 is a partial elevation and partial vertical section of the sleeve-like sectional member plastered into the end zone of a plaster bandage.

As shown in FIG. 5, the sectional element 10 is immoveably anchored by means of its knob-like engagement section 15 in the plaster bandage 20. Its folded-over closure 13 engages around the end-side closure edge 22 of the plaster sleeve 21. The knitted tube 30 lying between the plaster sleeve 21 and the plastered-in part of the body is guided on the end side over the folded-over closure 13 of the sectional element 10, a portion of the tube 30 engaging over the outer wall zone of the plaster sleeve 21. In this zone the knitted tube 30 is plastered in and therefore securely positioned, while the tube can exert its full effect in the remaining zone between the plaster sleeve 21 and the part of the body KT.

What is claimed is:

1. In a plaster bandage, a protective element for making the closure edges of the plastic bandage on a human body, comprising an axially extending sleeve-like flexible sectional element having an inside surface and an outside surface, said sectional element having a folded-over closure formed on one of the end edges thereof with said closure projecting outwardly from the outside surface of said sectional element, said closure extends for a slight length of said sectional element and has an arc-shaped surface extending outwardly from the outside surface of said sectional element with said arc-shaped surface having a convex surface facing in the opposite direction away from the opposite end of said sectional element and a concave surface facing in the direction toward the opposite end of said sectional element, said sectional element having a plurality of knob-like engagement sections formed thereon with said engagement sections projection outwardly from the outside surface of said sectional element, said sectional element is formed of a cross-linked toxicologically harmless silicone rubber, and the outside surface of said sectional element tapers inwardly toward the inside surface at the opposite end from the end forming said closure.

2. In a plaster bandage, as set forth in claim 1, including a knitted tube arranged to be positioned within said sectional element, said tube having an axial length sufficient to extend outwardly from both ends of said sectional element, said knitted tube extending axially from the end of said sectional element having said closure and said knitted tube being folded over in contact with the convex surface of said closure and extending toward the opposite end of said sectional element, and a plaster sleeve secured to the outside surface of said sectional element with said knitted tube secured to said plaster bandage.

* * * * *